United States Patent [19]

Dickey

[11] 4,027,789
[45] June 7, 1977

[54] FOAMING DEVICE FOR HIGH SOLIDS CONTENT FOAMABLE LIQUIDS

[75] Inventor: Clarence A. Dickey, Atlanta, Ga.

[73] Assignee: Glasrock Products, Inc., Atlanta, Ga.

[22] Filed: Sept. 10, 1975

[21] Appl. No.: 612,039

[52] U.S. Cl. ............................ 222/190; 222/211; 222/564; 239/343
[51] Int. Cl.² .................................... B65D 37/00
[58] Field of Search .......... 222/189, 190, 211–212, 222/215, 564; 239/327, 343, 370

[56] References Cited

UNITED STATES PATENTS

| 2,231,477 | 2/1941 | Palmer | 222/190 |
|---|---|---|---|
| 3,203,371 | 8/1965 | Mosey | 222/189 X |
| 3,422,993 | 1/1969 | Boehm et al. | 222/190 |
| 3,428,222 | 2/1969 | Wright | 222/190 X |
| 3,471,064 | 10/1969 | Micallef | 222/190 X |
| 3,709,437 | 1/1973 | Wright | 222/190 X |
| 3,937,364 | 2/1976 | Wright | 239/343 X |

Primary Examiner—Robert B. Reeves
Assistant Examiner—Charles A. Marmor
Attorney, Agent, or Firm—Lane, Aitken, Dunner & Ziems

[57] ABSTRACT

A foaming device for generating and dispensing foams formed by mixing air or other gas with a foamable liquid having a high solids content under pressures of a magnitude on the order of pressures developed by manual collapse of an elastomeric bottle. The device includes a continuous passageway extending from a point of submergence in liquid to be foamed through the gas to be mixed with the liquid to a discharge opening, that portion of the passageway located in the gas being formed of a porous tube by which gas under pressure will be introduced to liquid passing upwardly through the passageway under the same pressure and mixed therewith. A flow restriction in the form of a static mixer is located in the passageway at a point to be coextensive with or elevated above the level of the porous tube.

12 Claims, 4 Drawing Figures

FOAMING DEVICE FOR HIGH SOLIDS CONTENT FOAMABLE LIQUIDS

BACKGROUND OF THE INVENTION

This invention relates to improvements in foaming devices and more particularly, it concerns a low-cost foam generating and dispensing apparatus by which a foamable liquid having a relatively high solids content may be mixed with gas, such as air, and simultaneously dispensed as foam.

Since the introduction and popularization of aerosol dispensers, a wide variety of foam products have been available to the consuming public including, for example, cosmetics such as shaving creams, facial cleansing soaps and lotions, hair setting lotions and hair color foams; cleaning products such as upholstery cleaners, carpet shampoos, floor waxes and cleaners, furniture polishes and cleaners, and oven cleaners; medical products such as pain killers, burn treatments, antibiotic lotions and the like; and food products such as cake toppings, whipped desserts, salad dressings and various sauces. Because of the desirable characteristics of using these and many other products as a foam, in contrast to a liquid spray, and because of the ease with which aerosol dispensers may be handled, a substantial market has been generated for foamed or foamable products. Shortcomings of aerosol dispensers have been receiving considerable attention of late, however, such as the collective discharge of sufficient quantities of freon and other gases used in aerosol dispensers to have an adverse effect on the environmental quality of the atmosphere, increasing costs of materials required for aerosol containers and increasing manufacturing costs required for the fabrication, assembly and filling of aerosol dispensing units. As a result, manually operated dispensers are being looked to as a potential substitute for foamable products heretofore supplied only in pre-pressurized aerosol dispensers.

As compared with pressurized aerosol dispensers, manually operated foaming devices must be operated with limited and thus relatively low dispensing pressures. Provision must be made, therefore, for mixing air and foamable liquid under conditions which will produce foam of predictably uniform consistency such as by the forced collapse of a bottle containing air and the foamable liquid while maintaining resistance to dispensing flow at a minimum. Such conditions have been met in the past by discharging the air and foamable liquid through a porous element of material providing minute tortuous passages in which a highly turbulent flow of the liquid and air results in the appropriate mixing and homogenization of the discharged foam. See, for example, U.S. Pat. Nos. 2,680,010 issued June 1, 1954 to F. X. Dubay; 3,422,993 issued Jan. 21, 1969 to G. E. Boehm et al; and 3,709,437 issued Jan. 9, 1973 to H. E. Wright.

In a copending application of Jack C. Gardner, Ser. No. 584,610 filed June 6, 1975, now Pat. No. 3,985,271, and assigned to the assignee of the present invention, there is disclosed a manually actuated foaming device capable of generating and dispensing a highly consistent foam under pressures developed manually to displace foamable liquid and air directly through a porous member preferably formed of a sintered agglomerate of thermo-plastic particles. Because of its effectiveness in operation and also in light of its potential for low-cost manufacture, the foam generating and dispensing device disclosed in this copending application is believed to represent a viable substitute for pressurized aerosol dispensers particularly in connection with foamable liquid products having little or no solids content which would interfere with the passage of the liquid through the porous member.

Many of the foamable liquid products heretofore available in pressurized aerosol containers are known to contain a relatively high percentage of crystalline, fibrous or particulate solids. Floor and furniture waxers and polishers, for example, contain a substantial proportion of crystalline solids whereas food products are likely to contain a high fibrous solid content. Also, many cosmetic products contain a high percentage of particulate solids for fillers or for color pigments. The relatively sophisticated structure of pressurized aerosol containers as well as the relatively high gas pressures available in such dispensers have contributed to the avoidance of problems associated with a high solids content of the product to be foamed. The problem, however, is acute in connection with manually actuated foaming devices.

SUMMARY OF THE PRESENT INVENTION

In accordance with the present invention, a low pressure foaming device is provided in which a continuous passageway extending from a foam discharging nozzle through air to a supply of foamable liquid is established by successive tubular sections including the nozzle, a porous tube depending from the nozzle in an air space above the foamable liquid, and an imperforate dip tube connected at one end to the porous tube and having its other end submerged in the foamable liquid. A suitable obstruction to control liquid flow through the passageway, such as a static mixer in the nature of baffling capable of passing solids is located in the passageway at the level of the porous tubular section or above.

Thus, where the foaming device is incorporated in a cap assembly for a collapsible bottle or other receptacle containing air and foamable liquid, forcible collapse of the bottle will cause liquid to flow upwardly through the dip tube section of the passage to the porous tubular member through which air is simultaneously forced. The mixture of air and foamable liquid will then pass upwardly through the static mixing device in the passageway to be discharged through the nozzle as foam. Since the baffle means will pass solids which may exist in the liquid, the solids will not interfere with the mixing of the liquid and air.

Accordingly, among the objects of the present invention are: the provision of an improved foaming device capable of generating and dispensing foam by mixing air with a foamable liquid or mixture of foamable liquid and solids; the provision of such a foaming device which is readily adapted as a cap assembly for collapsible bottles or tubes of the type used in manually operated foaming devices; the provision of such a foaming device which will be unaffected in operation by the presence of solids in the liquid to be foamed; and the provision of such a foaming device which requires a minimal number of parts which are easily assembled to enable extremely low-cost manufacture.

Other objects and further scope of applicability of the present invention will become apparent from the detailed description to follow below taken in conjunction with the accompanying drawings in which like reference numerals designate like parts.

DETAILED DESCRIPTION OF THE PREFERRED EMBODIMENTS

Figure 1:
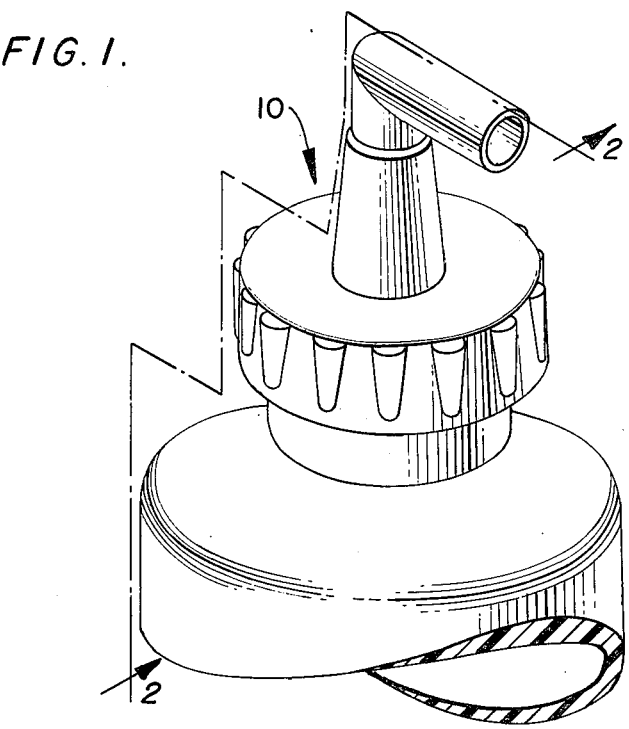
FIG. 1 is a fragmentary perspective view illustrating the exterior of a manually operated foaming device incorporating the present invention.
Figure 2:
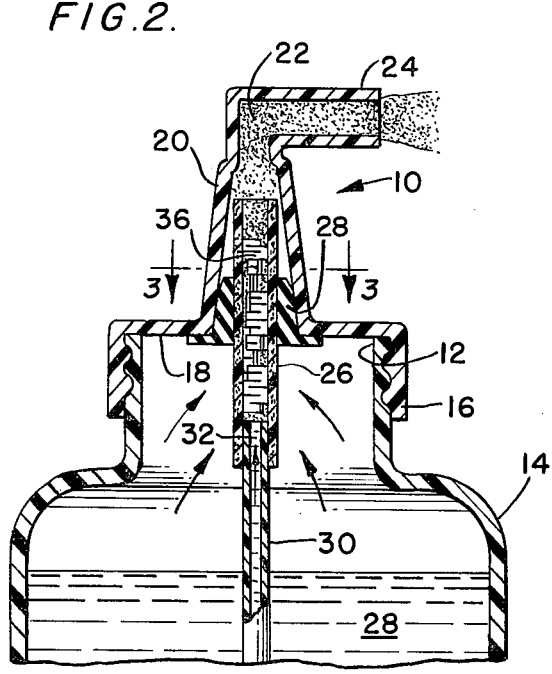
FIG. 2 is a cross-section taken on line 2—2 of FIG. 1.
Figure 3:
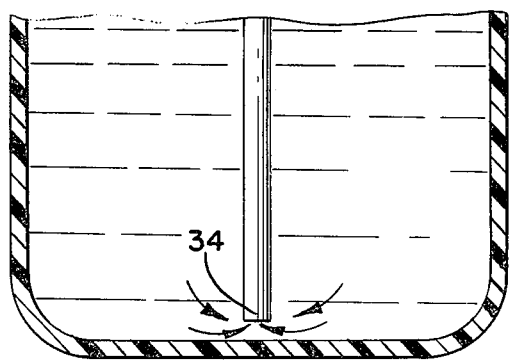
FIG. 3 is an enlarged cross-section taken on line 3—3 of FIG. 2.
Figure 3:
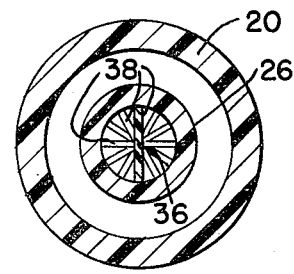

In FIGS. 1–3 of the drawings, one embodiment of the present invention is shown to be incorporated in a cap assembly, generally designated by the reference numeral 10, and adapted to be secured to the mouth 12 of a collapsible elastomeric bottle 14 by threaded cap skirt 16 in conventional fashion. The cap assembly is formed by a cap element 18 having in addition to the threaded skirt 16, an integral upstanding tubular formation 20 to establish a discharge passage 22 extending between the interior and exterior of the bottle 14. Although the configuration of the formation 20 may be varied from that shown for example in FIGS. 1 and 2, it is preferred that this formation include a horizontally disposed discharge nozzle 24 to facilitate the discharge of foam with the bottle 14 in the upright position as shown.

A porous, thin-walled tubular member 26 is supported from the interior end of the tubular formation 20 by suitable means such as an elastomeric grommet 28 so as to depend within the mouth 12 of the bottle as an extension of the discharge passageway 22. As shown in FIG. 2, the lower end of the porous tube 26 is positioned above the level of foamable liquid 28 in the bottle 14 so that it is exposed on its exterior exclusively to air. An imperforate dip tube 30 is secured at its upper end 32 preferably by thermal or ultrasonic fusion to the lower end of the porous tube 26 and extends to a lower open end 34 near the bottom of the bottle 14 so as to be fully submerged in the foamable liquid 28.

Positioned within the porous tube 26 and axially co-extensive therewith in this embodiment is an elongated restriction to liquid-solid flow through the tube 26 and passageway 22, such as for example, a static mixing device 36 capable of passing the liquid 28 including solids suspended therein. Although the specific structure of the static mixing element 36 may vary, as disclosed, the element is formed by a twisted ribbon of synthetic resinous material having a series of staggered and spaced severence lines extending respectively from opposite side edges so as to present a helical system of vertically oriented baffle elements 38 as shown in FIG. 3. In lieu of the static mixer 36, the obstruction to liquid flow through the passageway 22 may be formed as an irregular internal surface in the porous tube 26 or by other means to reduce the effective internal diameter of the passageway at or above the level of the tube 26 to achieve a desired air-liquid ratio in the foam product.

Although it is contemplated that a variety of porous materials may be used to form the tube 26, a material particularly well suited to use for the tube 26 is a sintered agglomerate of thermo-plastic particles of a type currently used in the formation of writing nibs for pens. Such materials are fully disclosed in U.S. Pat. No. 3,896,196 issued on July 22, 1975 to Clarence A. Dickey and John E. McDaniel and assigned to the assignee of the present invention. Although the disclosure of this patent is directed principally to the method for achieving a sintered agglomerate of spherical particles, the disclosure thereof also includes as exemplary prior art, description and illustration of sintered non-spherical thermo-plastic particles which, though possessing less desirable characteristics for use in the production of writing nibs, could be used in the porous tubular element 26 of the present invention for reasons of economy. The complete disclosure of the aforesaid issued patent is therefore incorporated by reference herein to provide an understanding of the material from which the tubular element 26 is preferably formed.

In light of the disclosure of the aforesaid U.S. patent, further detailed discussion of the material from which the porous element 26 may be formed is believed unnecessary herein except to note that the thermo-plastic material used may be any one of several resins such as polyethylene, polypropylene, polyvinyl alkylide as well as polyvinylidine fluoride mentioned in the aforementioned patent. Such porous polymeric structures may be easily molded or extruded to possess a void volume anywhere in the range of between 10% and 90% and a mean pore diameter in the range of 10 and 500 microns. Also it will be appreciated that because of the materials used in the formation of the porous tube 26, a wide selection of imperforate materials may be used in the formation of the dip tube 30 to facilitate its attachment directly by fusion to the porous member 26.

In the operation of the embodiment illustrated in FIGS. 1–3, assuming the bottle 14 to be partially filled with foamable liquid 28 as shown, the discharge of the liquid as a foam of predictably uniform consistency through the nozzle 24 is effected by manually collapsing the bottle 14 to impose a relatively low internal pressure on both the liquid 28 and the air in the bottle 14. As a result of the pressure, liquid will be forced upwardly through the dip tube 30 and simultaneously, air will be forced through the walls of the porous tubular member 26. The mixture of air and foamable liquid, as well as any solid materials entrained in the liquid, will pass upwardly through the static mixer 36. The resistance to liquid flow past the static mixer will be sufficient so that a desired proportion of air will be forced through the porous tube 26 and become entrained in the liquid to create a foam of uniform consistency in the discharge passage 22. Continued pressure will cause the discharge of foam from the nozzle 24. Upon release of the collapsing force on the bottle 14, air will return through the nozzle passage 22 and outwardly through the walls of the porous member 26 to the interior of the bottle. Inasmuch as the return of air along this path could be impeded by impregnation of the porous tubular member 26 with liquid and solids, it is contemplated that a separate return path may be provided by a one-way check valve in the cap assembly. An exemplary disclosure of an acceptable return air passageway of this type is found in a copending application of Jack C. Gardner, Ser. No. 584,609 filed June 6, 1975 now Patent No. 3,973,701, and also assigned to the assignee of the present invention.

Figure 4:
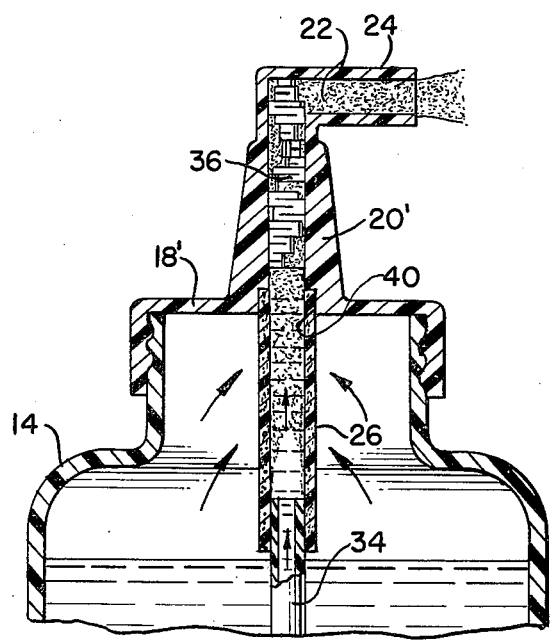
FIG. 4 is a fragmentary cross-section similar to FIG. 2 but illustrating an alternative embodiment of the present invention.

In an alternative embodiment of the invention as illustrated in FIG. 4, a modified cap element 18' is illustrated wherein the unstanding tubular formation 20' is provided with a counterbore 40 in its lower interior end to receive the tubular porous member 26 for support by thermal or fusion welding or by bonding. In this instance, the static mixer 36 extends upwardly in the passageway 22 from a lower end positioned above the porous tubular element 26. As a result, the entire length of the static mixer 36 is available for homogenization of the foam resulting from a mixture of air and liquid along the length of the porous tubular member 26. Also it will be appreciated that the assembly of the tubular porous member 26 and the cap element 18' in this embodiment is simplified by the elimination of the rubber grommet 28. The operation of the embodiment in FIG. 4 is to dispense foam from the nozzle 24 is identical to the embodiment of FIGS. 1–3.

Thus it will be seen that by this invention there is provided a highly effective foaming device by which the above-mentioned objectives are completely fulfilled. Not only is a direct passageway provided along the length of the dip tube 30, the porous tube 26 and the discharge passage 22 by which high solids content foamable liquids may be easily dispensed, but also the organization facilitates variations in the relative quantities of liquid and air to be intermixed in the foaming operation. In particular, the internal diameter of the dip tube, as well as the density of the mixing element, will be determinative of the quantity of liquid to be dispensed for a given pressure within the bottle 14. Because of the facility for regulation of pore size and void volume in the material from which the tube 26 is preferably formed, the quantity of air to be passed into the liquid under the same pressure may be selected to provide the desired foam consistency depending on the foaming characteristics of the specific liquid to be dispensed. Also by varying the length of the porous tube 26 and thus varying the surface area of the tubular member exposed to air, a further measure of control over the amount of air metered into the liquid is provided.

It will be appreciated further that various modifications and/or changes can be made in the disclosed embodiment without departure from the inventive concept manifested by those embodiments. It is expressly intended, therefore, that the foregoing description is illustrative of preferred embodiments only, not limiting, and that the true spirit and scope of the present invention be determined by reference to the appended claims.

I claim:

1. In a foaming device for mixing foamable liquid with a gas overlying the liquid and to dispense the mixture as a foam under pressure of a magnitude on the order of pressures developed by manual collapse of an elastomeric bottle adapted to contain the liquid and gas, the improvement comprising:
   means defining an imperforate foam discharge passageway;
   a tube having a continuous wall of porous material and depending from said means as an extension of said passageway to a lower end elevated above the level of foamable liquid to be dispensed;
   an imperforate dip tube depending from said porous tube as a further extension of said passageway to a lower end to be submerged in the foamable liquid; and
   an elongated static mixer in said passageway at or above the level of said porous tube said static mixer being operable to impede direct upward flow of liquid through said passageway and to insure foam generation by mixing of liquid with gas passing into said passageway through the wall of said porous tube along the length thereof and without passage of liquid outwardly through the porous tube wall.

2. The apparatus recited in claim 1 wherein said static mixer is positioned within and coextensive with said porous tube.

3. The apparatus recited in claim 1 wherein said static mixer is located above said porous tube in said passageway.

4. The apparatus recited in claim 1 wherein said porous tube is formed of a sintered agglomerate of thermo-plastic particles.

5. The apparatus recited in claim 4 wherein said sintered agglomerate possesses a void volume in the range of between 10% and 90% and has a mean pore diameter of between 10 and 500 microns.

6. The apparatus recited in claim 4 wherein said dip tube is also formed of a thermo-plastic material capable of heat fusion to said porous tube.

7. A foaming device for a collapsible bottle adapted to contain foamable liquid and air, said device comprising:
   a cap element attachable to the bottle and having a tubular formation to define a discharge passage extending between the interior and exterior of the bottle, said passage having an interior end to be positioned in air near the upper end of the bottle;
   a tubular member having a continuous porous wall secured to said cap member as a depending extension of said tubular formation and said passage;
   an imperforate dip tube having an upper end secured to said porous tubular member and depending as an extension of said passage to a lower open end to be submerged in liquid when said cap is attached to the bottle; and
   an elongated static mixer in said passage positioned axially therein above the upper end of said dip tube to impede upward flow of liquid through said passageway and to insure foam generation by mixing of liquid with gas passing into said passageway through the wall of said porous tubular member along the length thereof and without passage of liquid outwardly through the porous wall.

8. The apparatus recited in claim 7 wherein said static mixer is positioned to be coextensive with said porous tubular member.

9. The apparatus recited in claim 7 wherein said static mixer is positioned above said porous tubular member in said discharge passage.

10. The apparatus recited in claim 7 wherein said static mixer is defined by a twisted ribbon of synthetic resinous material having a series of staggered and spaced severence lines extending respectively from opposite side edges thereof so as to present a helical system of vertically oriented baffle elements in said passageway.

11. The apparatus recited in claim 7 wherein said tubular formation is shaped to establish a horizontal discharge nozzle portion in said discharge passage.

12. The apparatus recited in claim 7 wherein said porous tubular member is a sintered agglomerate of thermo-plastic particles, said dip tube being secured to said porous tubular member by fusion.

* * * * *